United States Patent
Picciano

(10) Patent No.: US 8,340,756 B2
(45) Date of Patent: Dec. 25, 2012

(54) ELECTRONIC STIMULATION DEVICE

(76) Inventor: Tony Picciano, Big Bear Lake, CA (US)

( * ) Notice: Subject to any disclaimer, the term of this patent is extended or adjusted under 35 U.S.C. 154(b) by 1115 days.

(21) Appl. No.: 12/185,882

(22) Filed: Aug. 5, 2008

(65) Prior Publication Data

US 2010/0036464 A1    Feb. 11, 2010

(51) Int. Cl.
*A61N 1/04* (2006.01)

(52) U.S. Cl. .......................................................... 607/2

(58) Field of Classification Search .............. 607/2, 116, 607/152
See application file for complete search history.

(56) References Cited

U.S. PATENT DOCUMENTS

| | | | |
|---|---|---|---|
| 3,601,126 A | 8/1971 | Estes | |
| 4,244,373 A | 1/1981 | Nachman | |
| 4,305,402 A * | 12/1981 | Katims | ........................ 600/554 |
| 4,349,030 A | 9/1982 | Belgard et al. | |
| 4,459,988 A | 7/1984 | Dugot | |
| 4,503,863 A | 3/1985 | Katims | |
| 4,510,939 A | 4/1985 | Brenman et al. | |
| 5,070,862 A | 12/1991 | Berlant | |
| 5,107,835 A | 4/1992 | Thomas | |
| 5,267,997 A | 12/1993 | Farin et al. | |
| 5,423,327 A | 6/1995 | Clauson et al. | |
| 5,776,173 A * | 7/1998 | Madsen et al. | ................... 607/67 |
| 5,944,747 A | 8/1999 | Greenberg et al. | |
| 6,289,245 B1 | 9/2001 | Mo et al. | |
| 7,110,826 B2 | 9/2006 | Motoi | |

* cited by examiner

*Primary Examiner* — Scott Getzow
*Assistant Examiner* — Amanda Patton
(74) *Attorney, Agent, or Firm* — Dovas Law, P.C.

(57) ABSTRACT

An electronic stimulation device is provided. The electronic stimulation device includes a wave generation device and a wave buffer connected to the wave generation device. A wave amplifier is connected to the wave buffer, and a transformer is connected to the wave amplifier. The transformer is configured for connection to leads for transmitting a current through a body of a user. The present invention further provides a method for providing electronic stimulation to a body of a user.

34 Claims, 10 Drawing Sheets

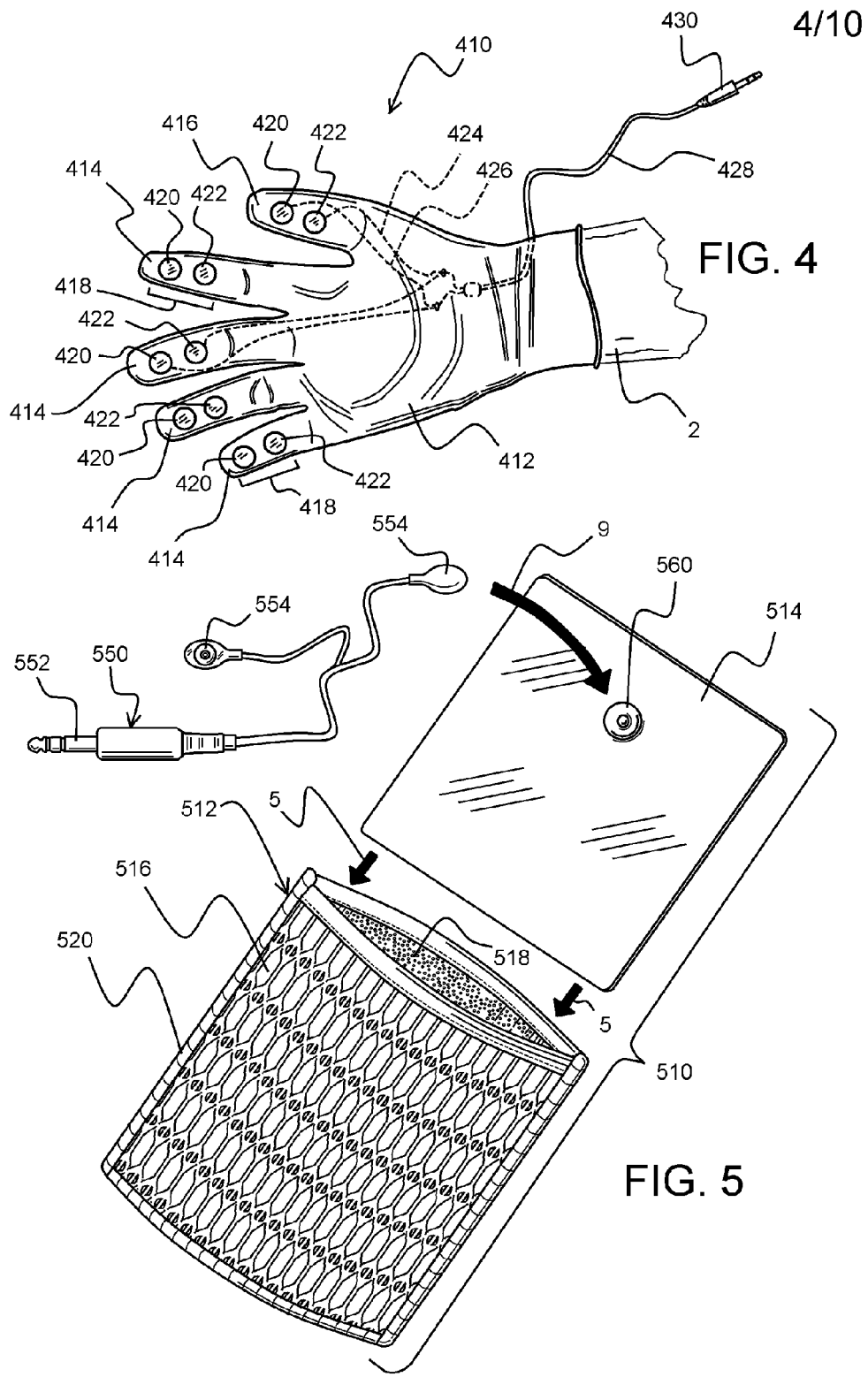

ELECTRONIC STIMULATION DEVICE

BACKGROUND

The flow of information within our body is achieved by the brains ability to generate electrical activity or specific signatures. The nervous system has the ability to orchestrate transmission of these complex electric signatures in order to achieve maximum communication directly with the muscle. These signatures, also known as nerve impulses or action potentials, represent a fundamental means of communication in the nervous system. An action potential propagates along the nerve in rapid bursts or specific frequency signatures. The motor neurons are able to recognize these specific frequency signatures as muscle contraction signatures and cause the muscle to contract. It would be desirable to resonate the specific frequency signatures sent from the brain to the motor nerve and cause a muscle contraction as seen with physical activity and or regular exercise.

In general, aging cells become progressively less able to form and maintain tissue. The symptoms we see associated with aging cells are skin atrophy and wrinkled deteriorating skin also know as human aging. Aging cells may not be clueless about their life span. Recent studies show they have a "clock" that reminds them of passing time so that they can achieve essential goals before it is too late. Normal human cells replicate a limited number of times before they reach "replicative senescence" and stop dividing. At this point the cells are still alive, breathing and metabolizing food, sometimes for months, until they die. The "molecular clock" that informs the cell of its limited life span is the telomere, a structure at the end of each chromosome that shortens with each cell division. Eventually, the cell must yield to a fate of a limited number of divisions and then die. It would further be desirable to uses specific signals to achieve communication at the cellular level with the purpose of increasing cell life span and/or increase cellular performance.

SUMMARY

The present invention provides an electronic stimulation device. The electronic stimulation device includes a wave generation device and a wave buffer connected to the wave generation device. A wave amplifier is connected to the wave buffer, and a transformer is connected to the wave amplifier. The transformer is configured for connection to leads for transmitting a current through a body of a user.

The present invention further provides a method for providing electronic stimulation to a body of a user. The method includes providing a wave generation device. An amplifier is connected to the wave generation device, and a current limiting transformer is connected to the amplifier. A shaped wave is generated with the wave generation device, and the shaped wave is amplified with the amplifier. The current limiting transformer is used to produce a transformed wave, and the transformed wave is applied to a body of a user.

BRIEF DESCRIPTION OF THE DRAWING(S)

The foregoing Summary as well as the following detailed description will be readily understood in conjunction with the appended drawings which illustrate preferred embodiments of the invention. In the drawings:

FIG. 4 is a plan view of a first wave application device according to a preferred embodiment of the present invention.

FIGS. 5 and 6 are perspective views of a second wave application device according to a preferred embodiment of the present invention.

DETAILED DESCRIPTION OF THE PREFERRED EMBODIMENT(S)

Figure 1:
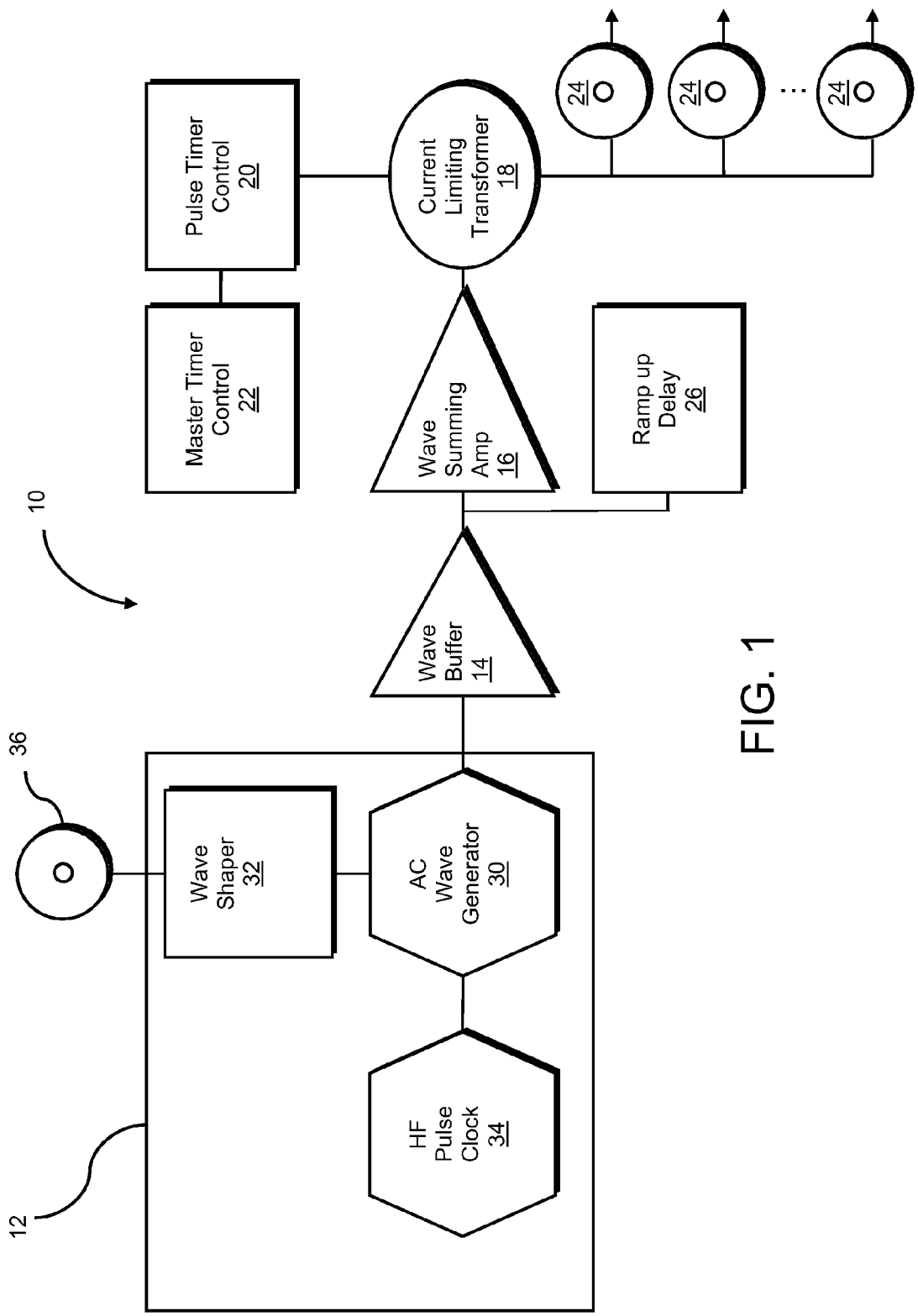
FIG. 1 is a diagram showing an electronic stimulation device according to a first preferred embodiment of the present invention.

Certain terminology is used in the following description for convenience only and is not limiting. The words "right," "left," "top," and "bottom" designate directions in the drawings to which reference is made. The words "a" and "one" are defined as including one or more of the referenced item unless specifically stated otherwise. This terminology includes the words above specifically mentioned, derivatives thereof, and words of similar import. The phrase "at least one" followed by a list of two or more items, such as A, B, or C, means any individual one of A, B or C as well as any combination thereof.

The preferred embodiments of the present invention are described below with reference to the drawing figures where like numerals represent like elements throughout.

Referring to FIG. 1, a diagram of an electronic stimulation device 10 for applying electrical waves to the body of a user according to a first preferred embodiment of the present invention is shown. The electronic stimulation device 10 includes a wave generation device 12, a wave buffer 14 connected to the wave generation device 12, a wave amplifier 16 connected to the wave buffer 14, and a transformer 18 connected to the wave amplifier 16. The transformer 18 is configured for connection to leads for transmitting a current through a body of a user. A pulse timer control 20 is connected to the transformer 18 for selectively setting an on and off duration of a wave output by the transformer 18.

The wave generation device 12 is preferably configured to produce one or more of square waves, modified square waves, rectangular waves, leading edge buffered waves, and pulses, which waves are transmitted to the wave buffer 14. The frequencies of the waves produced by the wave generation device 12 are preferably less than about 2000 Hz, more preferably between about 150 Hz and 1500 Hz, and most preferably between about 200 Hz and 1260 Hz.

The wave amplifier 16 is preferably a wave summing amplifier configured to raise the voltage of a shaped wave received from the wave generation device 12. Preferably the voltage of the shaped wave is raised by a factor of about 2 to about 12 volts AC RMS by the wave amplifier 16. An example of a preferred component of the wave summing amplifier is model number TDA2040, 20 Watt Hi-Fi Audio Power Amplifier, manufactured by ST Microelectronics Inc. The wave buffer 14 is configured to receive feedback from the wave amplifier 16 for maintaining wave morphology of a shaped wave generated by the wave generation device 12.

The wave buffer 14 preferably includes a diode matrix buffer. Preferably the diode matrix buffer of the wave buffer 14 includes a model number BC184C transistor, manufactured by Fairchild Semiconductor Corporation, San Jose, Calif. The base of the BC184C transistor is preferably configured to feedback to the emitter of the transistor BC184C via a triple diode matrix, including 3 diodes configured in series between the base and the emitter. Alternatively, any comparable transistor may be used in place of the BC184C transistor. Preferably, a cathode of a diode of the triple diode matrix first in order from the base of the BC184C transistor is connected to the wave generation device 12 to buffer the signal from the wave generation device 12.

A ramp up delay 26 is preferably connected to the wave buffer 14 for the purpose of increasing the amplitude of the signal by implementing a time delay. Preferably the ramp up delay includes an electrolytic capacitor, rated at about 220 μf and 35 volts, connected to a signal diode, for example a model 1N914 signal diode, manufactured by Vishay Intertechnology, Inc., Malvern, Pa.

The transformer 18 is preferably configured to increase the voltage of a wave transmitted by the amplifier 16 to the transformer 18 by a factor of between about 40 and about 60 times and is preferably a current limiting transformer configured to limit the current amplitude output to about 1000 microamperes. More preferably, the transformer 18 is a current limiting transformer configured to limit current amplitude output to less than about 350 microamperes. Most preferably, the transformer 18 is a current limiting transformer configured to limit current amplitude output to less than about 300 microamperes. Current limiting is preferably achieved by the transformer 18 through the use of a tightly coupled, magnetically saturable iron core. The iron core provides resistance to a fluctuating magnetic field which, in turn, impedes current flow. The result is a regulated current even under direct short of an output stage. Such a configuration is important for the electrical safety of the electronic stimulation device 10.

The wave generation device 12 comprises an AC wave generator 30, a wave shaper 32 connected to the AC wave generator 30 for designating a wave shape, and a pulse clock 34 connected to the AC wave generator for timing a designated wave. The AC wave generator 30 preferably includes a dual divider including a flip-flop, for example a model CD4013B dual D flip-flop manufactured by National Semiconductor Corporation, Santa Clara, Calif. The pulse clock 34 preferably includes one or more timer circuits, for example a model LM556c dual timer manufactured by National Semiconductor Corporation. The wave shaper 32 is preferably a multiplexer which includes a diode resistor matrix.

The wave generation device 12 preferably operates in the following manner. The pulse clock 34 operating from a DC power supply sets a wavelength pattern by outputting pulses to the wave generator 30 at approximately 400 Hz or other suitable frequency, setting the necessary timing for the device 12. The wave generator 30, which is preferably a dual divider including a flip-flop as indicated above, preferably creates a square wave which alternates from positive to negative potential. The wave shaper 32 in conjunction with the wave buffer 14 modifies the square wave giving it form and a desired leading edge morphology. The wave frequency is user adjustable using a frequency selector switch 36 as described below. A preferred wave generation device 12 uses the above-indicated LM556c dual timer which outputs pulses to set desired wavelengths. These pulses provide the clock frequency for the above-described CD4013B dual D flip-flop. The specific frequencies and signatures are adjusted by varying the trigger voltage to the LM556c dual timer via the frequency selector switch 36.

The frequency selector switch 36 is connected to the wave generation device 12 for adjusting the frequency of a wave output by the wave generation device 12. The frequency selector switch 36 is preferably configured to set the output of the wave to generally discrete predetermined frequencies. The predetermined frequencies are preferably within a range of less than about 2000 Hz as indicated above. More preferably, the frequency selector switch 36 permits selection of discrete frequencies within a predetermined range between 150 Hz and 1500 Hz. Most preferably, the frequency selector switch 36 permits selection of discrete frequencies within a predetermined range between 200 Hz and 1260 Hz. A test system which achieved desirable results implemented five (5) discrete settings including 201.0 Hz, 402.9 Hz, 603.9 Hz, 1004 Hz and 1256 Hz, respectively corresponding to wave periods of 4.963 milliseconds, 2.484 milliseconds, 1.657 milliseconds, 0.996 milliseconds, 0.796 milliseconds.

Figure 9A:
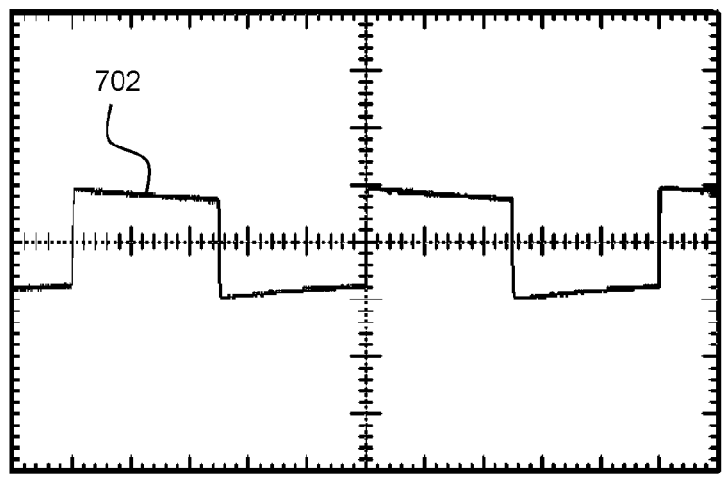
FIGS. 9A-9E are diagrams showing preferred wave forms produced by the electronic stimulation device of FIG. 1.
Figure 9B:
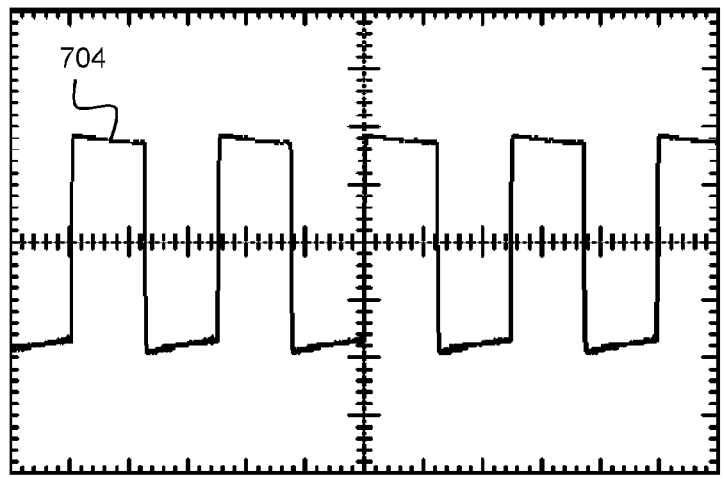
Figure 9C:
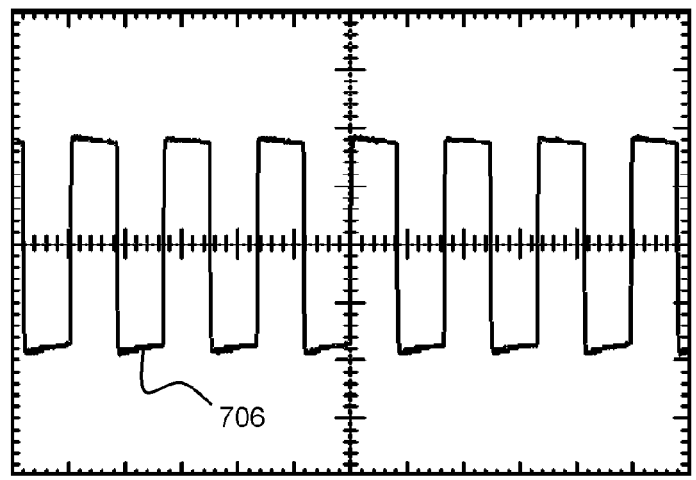
Figure 9D:
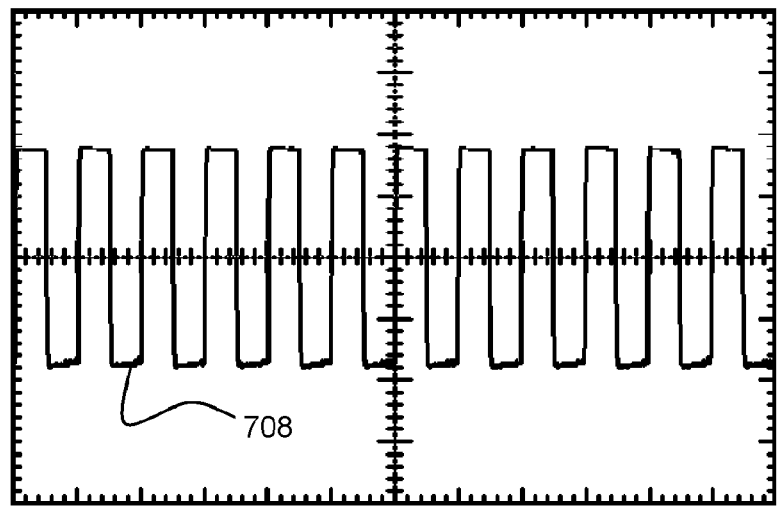
Figure 9E:
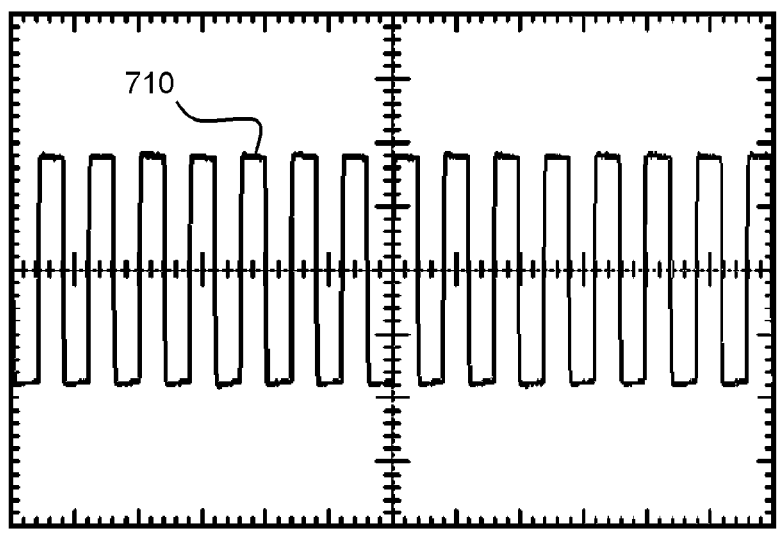

FIGS. 9A-9E show wave forms generated by the wave generation device 12 as output by the transformer 18. These wave forms represent preferred square wave morphologies at given frequencies for achieving desired health effects. FIG. 9A shows a modified square wave at 200 Hz 702 which may be effective in promoting muscle building. FIG. 9B shows a modified square wave at about 400 Hz 704 which may be effective in promoting inch loss. FIG. 9C shows a modified square wave at about 600 Hz 706 which may be effective in promoting skin firming. FIG. 9D shows a modified square wave at about 1000 Hz 708 which may be effective in promoting skin toning. FIG. 9E shows a modified square wave at about 1250 Hz 710 which may be effective in promoting cellulite reduction.

A pulse timer control 20 is preferably connected to the transformer 18 to pulse the wave output from the transformer 18 on and off for predetermined durations. A master timer control 22 is provided connected to the pulse timer control 20 to permit a user to set desired durations for on and off periods, and to set a total session duration of a treatment period. Preferably, a pulse duration of less than ten (10) seconds on and less than ten (10) seconds off may be set using the pulse timer control 20, and a total session duration of one (1) minute to two hundred (200) minutes may be set using the master timer control 22. More preferably, a duration of less than six (6) seconds on and less than six (6) seconds off may be set by the pulse timer control 20. Preferably, based on a user's preference, the on duration setting may be of the same time value as or different time value than that of the off duration. The pulse timer control 20 may be of any suitable type. The master timer control 22 may be of any suitable type, for example a 716 series electronic timer, manufactured by Fritz Kübler Gmbh, Villingen-Schwenningen, Germany.

Voltage controllers 24 are preferably provided to permit a user to control the voltage amplitude of a wave output by the current limiting transformer 18. The voltage controllers 24 are preferably potentiometers, and more preferably 5000 Ohm potentiometers configured to limit the wave output between 0 and 125 volts AC RMS. Wave application devices as shown in FIGS. 4-7 and described in detail below may be connected to the output of the voltage controllers 24 to permit application of a plurality of waves of differing amplitude through the body of a user.

An example of a preferred mode of producing an AC wave using the electronic stimulation device 10 is described as follows with reference to the above-described components. The frequency selector switch 36 preferably provides about 15V electric potential to the diode resistor matrix of the wave shaper 32. The diode resistor matrix provides a predetermined voltage to a trigger input of the LM556c dual timer of the pulse clock 34 to set the pulses needed for a desired wavelength which is produced by the CD4013B dual D flip-flop of the wave generator 30. The wave from the CD4013B dual D flip-flop is buffered via the BC184C transistor and the triple diode matrix of the wave buffer 14. The wave enters the TDA2050 amplifier of the wave amplifier 16 in which the wave amplitude and shape is determined by the value of a resistor connected to pins 2 and 4 of the TDA2050 amplifier. The wave then enters the transformer 18 which preferably steps up voltage and drops current by approximately 40 to 60 times resulting in the final wave value. The potentiometer of the voltage controller 24 limits the potential of the wave output to a user selected level. The current may be applied through a body of user via leads connected to one or more of the voltage controllers 24.

Figure 2:
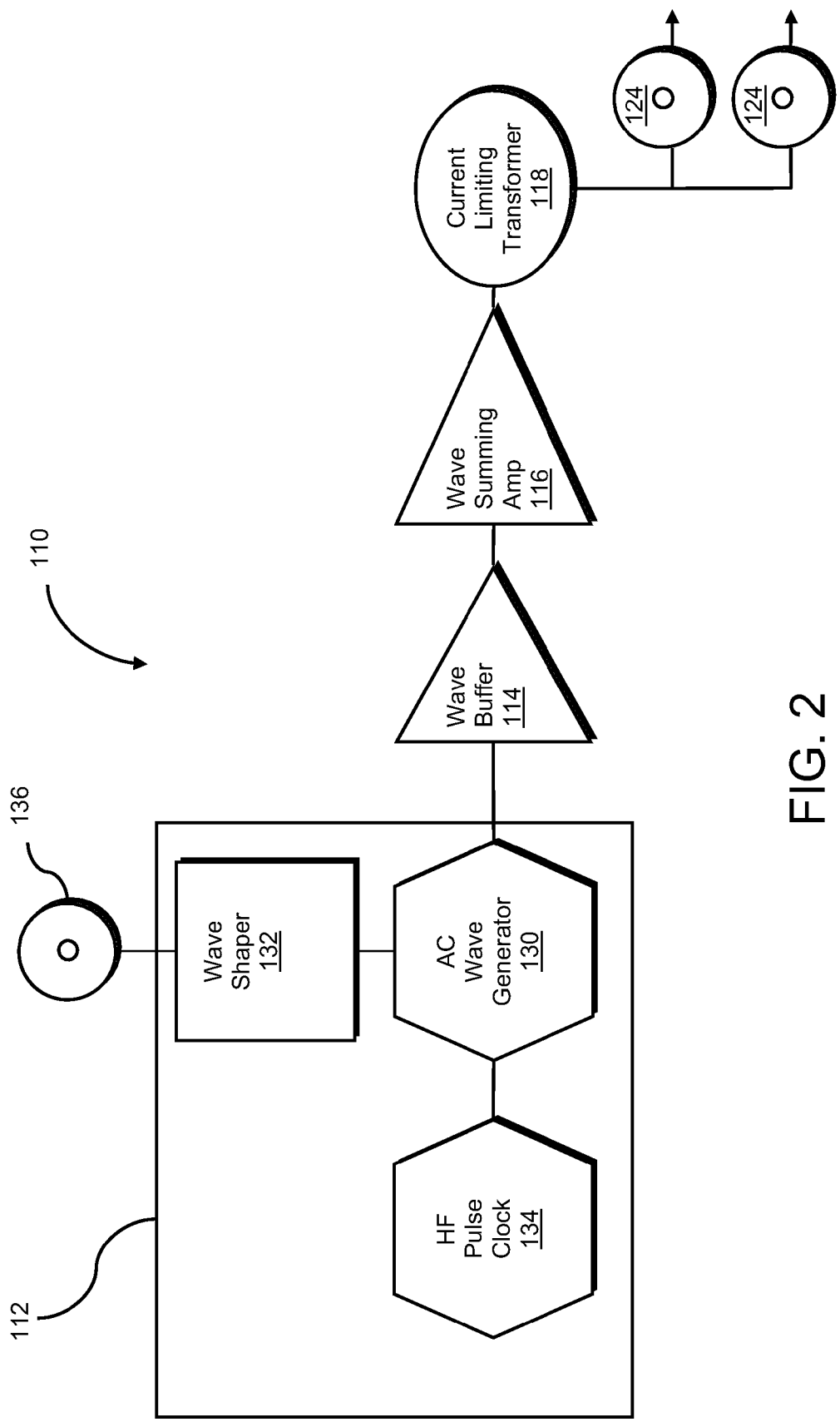
FIG. 2 is a diagram showing an electronic stimulation device according to a second preferred embodiment of the present invention.

Referring to FIG. 2, a diagram of an electronic stimulation device 110 for applying electrical waves to the body of a user according to a second preferred embodiment of the present invention is shown. The electronic stimulation device 110 includes a wave generation device 112, a wave buffer 114 connected to the wave generation device 112, a wave amplifier 116 connected to the wave buffer 114, and a transformer 118 connected to the wave amplifier 116. The transformer 118 is configured for connection to leads for transmitting a current through a body of a user via voltage controllers 124.

The wave generation device 112 is preferably configured to produce one or more of square waves, modified square waves, rectangular waves, leading edge buffered waves, pulses, and alternating positive-negative pulses, which are transmitted to the wave buffer 114. The frequencies of the waves produced by the wave generation device 112 are preferably less than about 2000 Hz, more preferably less than 1200 Hz, and most preferably between about 20 Hz and 1000 Hz.

The wave buffer 114 is configured to receive feedback from the wave amplifier 116 for maintaining wave morphology of a shaped wave generated by the wave generation device 112. The wave buffer 114 is preferably a diode matrix buffer. Preferably, the diode matrix buffer of the wave buffer 114 includes a model number BC184C transistor, manufactured by Fairchild Semiconductor Corporation, of San Jose, Calif. The base of the transistor BC184C is configured to feedback to the emitter of the transistor BC184C via a triple diode matrix, including 3 diodes configured in series between the base and the emitter. Alternatively, any suitable transistor other than the BC184C transistor may be used. Preferably, a cathode of the diode in the triple diode matrix first in order from the base of the transistor is connected to the wave generation device 112 to buffer the signal from the wave generation device 112. In addition, a resistor, preferably an approximately 100 Ohm resistor, is preferably tied to the cathode of the first diode to ground for the purpose of limiting current and voltage amplitude.

The wave generation device 112 is preferably configured to deliver a wave to the wave buffer 114. The wave amplifier 116 is preferably a wave summing amplifier configured to raise the voltage of a shaped wave received from the wave generation device 112 through the wave buffer 114. Preferably the voltage of the shaped wave is raised by a factor of about 2.4 to about 0.5 volts AC RMS by the wave amplifier 116. An example of a suitable wave summing amplifier is model number TDA2050, 32 Watt Hi-Fi Audio Power Amplifier, manufactured by ST Microelectronics Inc.

The transformer 118 is preferably configured to increase the voltage of a wave transmitted by the amplifier 116 to the transformer 118 by a factor of between about 5 and about 50 times. The transformer 118 is preferably a current limiting transformer configured to limit the current amplitude output to about 1000 nanoamperes. More preferably, the transformer 118 is a current limiting transformer configured to limit current amplitude output to less than about 900 nanoamperes. Most preferably, the transformer 118 is a current limiting transformer configured to limit current amplitude output to less than about 850 nanoamperes.

Like the wave generation device 12 of the first preferred embodiment, the wave generation device 112 comprises an AC wave generator 130, a wave shaper 132 connected to the AC wave generator 130 for designating a wave shape, and a pulse clock 134 connected to the AC wave generator 130 for timing a designated wave. The AC wave generator 130 preferably includes a dual divider including a flip-flop, for example the CD4013B dual D flip-flop manufactured by National Semiconductor Corporation of Santa Clara, Calif. The pulse clock 134 preferably includes one or more timer circuits, for example the LM556c dual timer manufactured by National Semiconductor Corporation. The wave shaper 132 is preferably a multiplexer which includes a diode resistor matrix.

The wave generation device 112 preferably operates in the following manner. The pulse clock 134 operating from a DC power supply sets a wavelength pattern by outputting pulses to the wave generator 130 at approximately 400 Hz or other suitable frequency, setting the necessary timing for the device 112. The wave generator 130, which is preferably a dual divider including a flip-flop as indicated above, creates a square wave which alternates from positive to negative. The wave shaper 132 in conjunction with the wave buffer 114 modifies the square wave giving it form and a desired leading edge morphology. The wave frequency is user adjustable using a frequency selector switch 136 as described below.

The frequency selector switch 136 is connected to the wave generation device 112 for adjusting the frequency of a wave output by the wave generation device 112. The frequency selector switch 136 is preferably configured to set the output of the wave to the wave buffer 14 to desired predetermined frequencies. The predetermined frequencies are preferably within a range of less than about 2000 Hz as indicated above. More preferably, the frequency selector switch 136 permits selection of a discrete number of frequencies within a predetermined range between 0 Hz and 1200 Hz. Most preferably, the frequency selector switch 136 permits selection of a discrete number of frequencies within a predetermined range between 20 Hz and 1100 Hz. A test system which achieved desirable results implemented five (5) discrete settings including 20 Hz, 500 Hz, 900 Hz, 1000 Hz and 1100 Hz, respectively corresponding to wave periods of 50.0 milliseconds, 2.0 milliseconds, 1.1 milliseconds, and 1.0 milliseconds.

Voltage controllers 124 are provided to permit a user to control the voltage amplitude of a wave output by the current limiting transformer 118. Voltage controllers 124 preferably each include a potentiometer, and more preferably a 5K Ohm potentiometer, configured to limit the wave output between about 0 and 20 volts AC RMS. Wave application devices as shown in FIGS. 4-7 and described in detail below may be connected to the output of the voltage controllers 124 to permit application of a plurality of waves of differing amplitude through the body of a user.

Figure 10A:
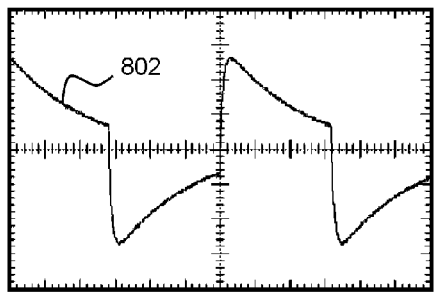
FIGS. 10A-10F are diagrams showing preferred wave forms produced by the electronic stimulation device of FIG. 2.
Figure 10B:
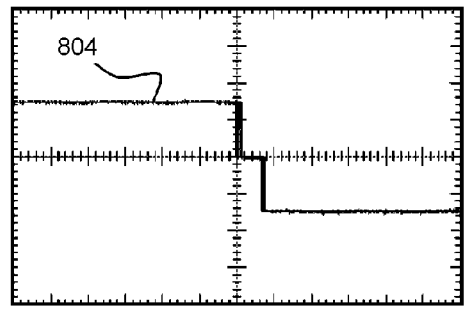
Figure 10C:
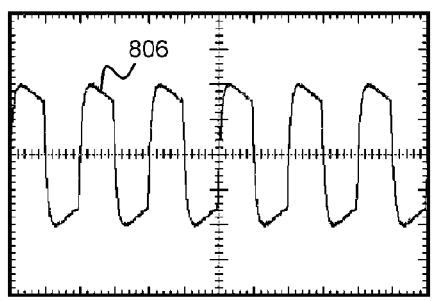
Figure 10D:
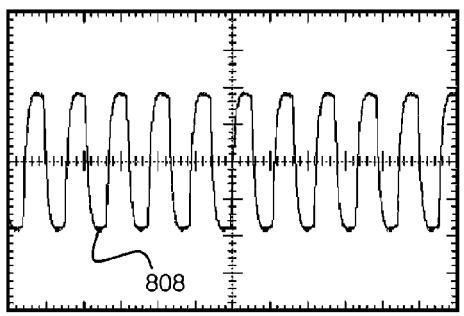
Figure 10E:
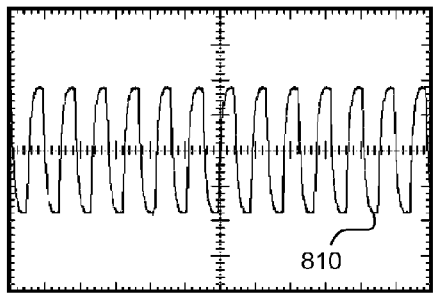
Figure 10F:
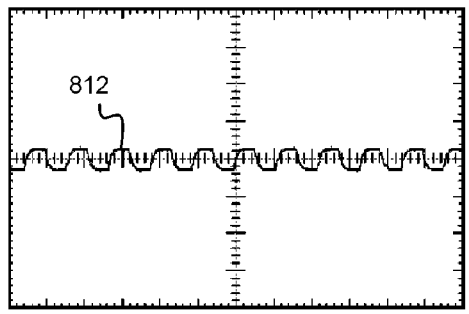

FIGS. 10A-10F show wave forms generated by the wave generation device 112 as output by the transformer 118 for application to the body of a user via the voltage controllers 124. FIG. 10A shows a complex modified square wave at a frequency of 40 Hz 802 which may be effective in promoting skin oxygenation. FIG. 10B shows an extended pulse 804 which alternates from positive 8.5 volts DC to negative 8.5 volts DC, having a frequency of 2.5 Hz corresponding to a period of about 0.40 seconds, which may be effective in promoting skin tightening. FIG. 10C shows a complex modified square wave at a frequency of 500 Hz 806 which may be effective for promoting deep tissue toning. FIGS. 10D, 10E and 10F show complex modified square waves at 900 Hz, 1100 Hz, and 1000 Hz 808, 810, 812 respectively which may be effective for promoting superficial skin refinement.

An example of a preferred mode of producing an AC wave using the electronic stimulation device 110 is described as follows with reference to the above-described components. The frequency selector switch 136 preferably provides about 15V electric potential to the diode resistor matrix of the wave shaper 132. The diode resistor matrix provides a predetermined voltage to a trigger input of the LM556c dual timer of the pulse clock 134 to set the pulses needed for the desired wavelength produced by the CD4013B dual D flip-flop of the wave generator 130. The wave from the CD4013B dual D flip-flop is buffered via the BC184C and the triple diode matrix of the wave buffer 114. The wave enters the TDA2050 amplifier of the wave amplifier 116 in which the wave amplitude and shape is determined by the value of a resistor connected to pins 2 and 4 of the TDA2050 amplifier. The wave then enters the transformer 118 which preferably steps up voltage and drops current by approximately 5 to 50 times resulting in the final wave value. The potentiometer of the voltage controller 124 limits the wave output to a user selected level. The current may be applied through a body of user via leads connected to one or more of the voltage controllers 124.

Figure 3:
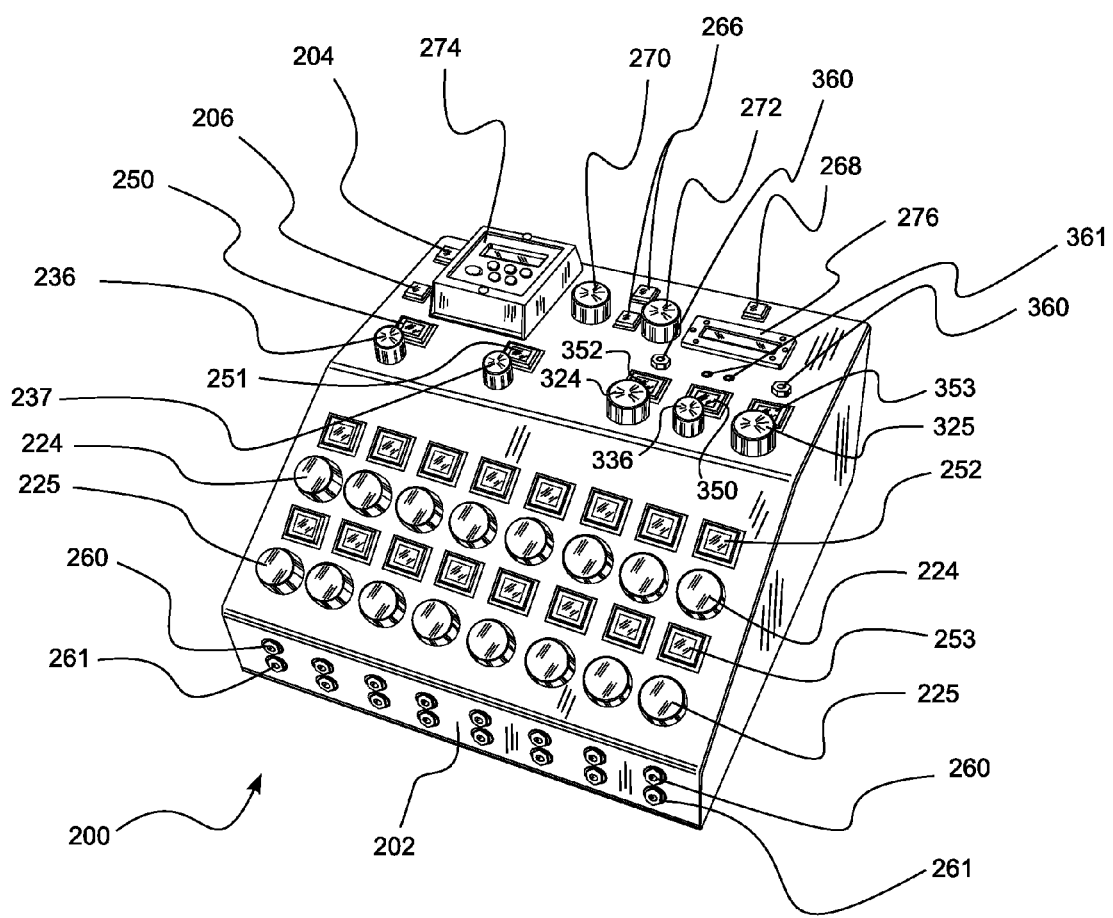
FIG. 3 is a perspective view of a unit configured to house the electronic stimulation devices according to the first and second preferred embodiments of the present invention.

Referring to FIG. 3, an electronic stimulation apparatus 200 configured to house the electronic stimulation devices 10 and 110 as described above is shown. Preferably, the electronic stimulation apparatus 200 houses two independently controllable electronic stimulation devices 10 according to the first preferred embodiment of the present invention and an electronic stimulation device 110 according to the second preferred embodiment of the present invention. The electronic stimulation apparatus 200 includes a housing 202 to which a number of control switches and displays are mounted. A power switch 204 controls power to the first and second preferred electronic stimulation devices 10, 110. A start-stop switch 206 is configured to start and stop application of electronic stimulation while power to the electronic stimulation devices 10, 110 remains on.

A first frequency selection dial 236 is connected to the frequency selector switch 36 of a first one of the first preferred electronic stimulation devices 10 shown in FIG. 1 to control a wave frequency output by the first one of the electronic stimulation devices 10. A second frequency selection dial 237 is connected to the frequency selector switch 36 of a second one of the first preferred electronic stimulation devices 10. As indicated above, the frequency selector switch 36 is preferably configured to provide five selectable preset frequencies. Voltage controller dials 224 aligned in a single row on the housing 202 are connected to the voltage controllers 24 of the first one of the electronic stimulation devices 10 to provide voltage amplitude adjustment to individual corresponding ones of stereo outputs 260 aligned in a single row on the housing 202. Voltage controller dials 225 aligned in a single row on the housing 202 are connected to the voltage controllers 24 of the second one of the electronic stimulation devices 10 to provide voltage amplitude adjustment to individual corresponding ones of stereo outputs 261 aligned in a single row on the housing 202. Accordingly, each row of outputs 260, 261 corresponds to a different one of the electronic stimulation devices 10 such that each of the eight outputs 260 share a frequency during operation, and each of the eight outputs 261 share a frequency during operation, while the voltage amplitude of each output 260, 261 may be independently controlled via the respective voltage controller dials 224, 225. Displays 250, 251 provide a visual indication of the respective frequencies selected by the frequency selection dials 236, 237. Displays 252, 253 provide a visual indication of the respective voltage amplitudes selected by the voltage controller dials 224, 225. Displays 250, 251, 252, 253 are preferably LCD displays. An impedance meter 276 is preferably connected to the outputs 260, 261 for providing an indication of the impedance through the body of a user.

A third frequency selection dial 336 is connected to the frequency selector switch 136 of the second preferred electronic stimulation devices 110 to control a wave frequency output by the electronic stimulation device 110 to stereo outputs 360 and paired mono outputs 361. Voltage controller dial 324 is connected to a voltage controller 124 of the electronic stimulation device 110 to provide voltage amplitude adjustment to the stereo outputs 360. Voltage controller dial 325 is connected to another voltage controller 124 of the electronic stimulation device 110 to provide voltage amplitude adjustment to the mono outputs 361. Displays 350 provide a visual indication of the frequency selected by the frequency selection dial 336. Displays 352, 353 provide a visual indication of the respective voltage amplitudes selected by the voltage controller dials 324, 325.

Device selection switches 266 permit power toggling between the first preferred electronic stimulation devices 10 and the second preferred electronic stimulation device 110 such that the devices 10, 110 may not be simultaneously activated. A visual indicator 268 indicates when the second preferred device 110 is activated. A rest time adjustment dial 270 is connected to both the pulse timer controls 20 of the first preferred electronic stimulation devices 10 and the pulse timer control 120 of the second preferred electronic stimulation device 110 for setting a duration of the off time of a wave output by the respective transformers 18, 118. Preferably off time may be set using the rest time adjustment dial 270 for discrete time intervals between 1 seconds and 6 seconds. On time adjustment dial 272 is connected to both the pulse timer controls 20 of the first preferred electronic stimulation devices 10 and the pulse timer control 120 of the second preferred electronic stimulation device 110 for setting a duration of the on time of a wave output by a respective transformer 18, 118. Preferably, on time may be set using the application time adjustment dial 272 for discrete time intervals between 1 seconds and 6 seconds. A master timer interface 274 is connected to the master timer controls 22 of the first preferred electronic stimulation devices 10 and the master timer control 122 of the second preferred electronic stimulation device 110 for setting a total session time during which the respective transformers 18, 118 provide on and off cycling of a wave output. Preferably, total session time may be set for any desired period using the master timer interface 274, for example a total session time of one (1) minute to two hundred (200) minutes. The electronic stimulation devices 10, 110 included with the electronic stimulation apparatus 200 may alternatively share one or more pulse timer controls 20, 120, master timer controls 22, 122, or other components for the purpose of architecture efficiency and manufacturing cost savings.

Referring to FIG. 4, a first wave application device 410 is shown suitable for connection to the electronic stimulation apparatus 200 for delivering electric waves from one or both of the electronic stimulation devices 10, 110. The first wave application device 410 comprises a glove 412 fabricated of an insulating material shown as worn on the right hand of a user 2 in FIG. 5. Preferably the glove 412 is fabricated from a synthetic fabric material including neoprene. Alternatively, any suitable material including for example butyl rubber may be used in forming the glove 412. The glove includes four fingers 414 and a thumb 416. Contact element pairs 418 including first contact elements 420 and second contact elements 422 are provided on each finger 414 and the thumb 416 of the glove 412. Each of the contact element pairs 418 are connected to a lead pair including a first lead conduit 424 and a second lead conduit 426. For each of the contact element pairs 418, the first lead conduit 424 is connected to the first contact element 420 and the second lead conduit 426 is connected to the second contact element 422. The first and second lead conduits 424, 426 are connected to a stereo connector 430 through a lead wire 428. The lead wire 428 is preferably a medical grade cable with a suitable thermoplastic elastomer surround including Santoprene™ or other suitable polymer.

The stereo connector 430 is connectable to either of the above-described electronic stimulation devices 10, 110 for conducting a current in the form of a wave between the contact element pairs 418 through a portion of the body of a user touched by the first and second contact elements 420, 422. In a preferred mode of use, the stereo connector 430 may be connected to the stereo outputs 360 of the electronic stimulation apparatus 200 to provide current output limited to about 1000 nanoamperes or less through the current limiting transformer 118 of the second preferred electronic stimulation device 110. A user wearing the glove 412 may apply the contact element pairs 418 to a face or other portion of a body of the user or of another person in a therapy procedure, sending current between the first contact element 420 and the second contact element 422 through that portion of the body.

Figure 6:
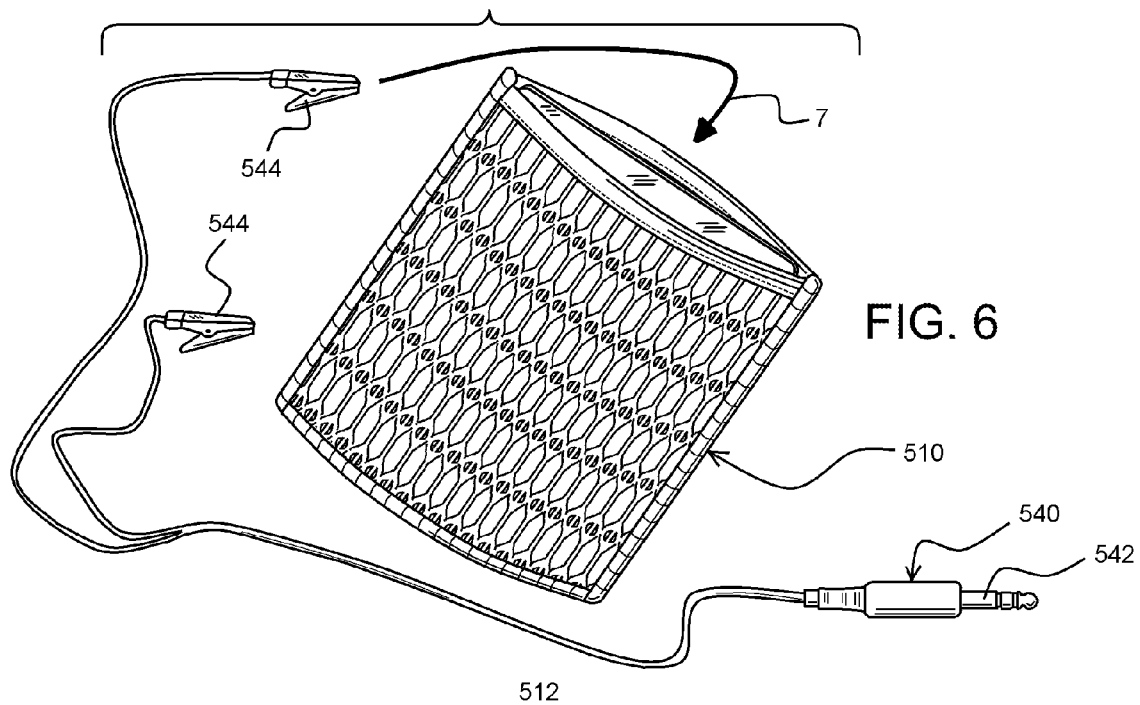
Figure 7:
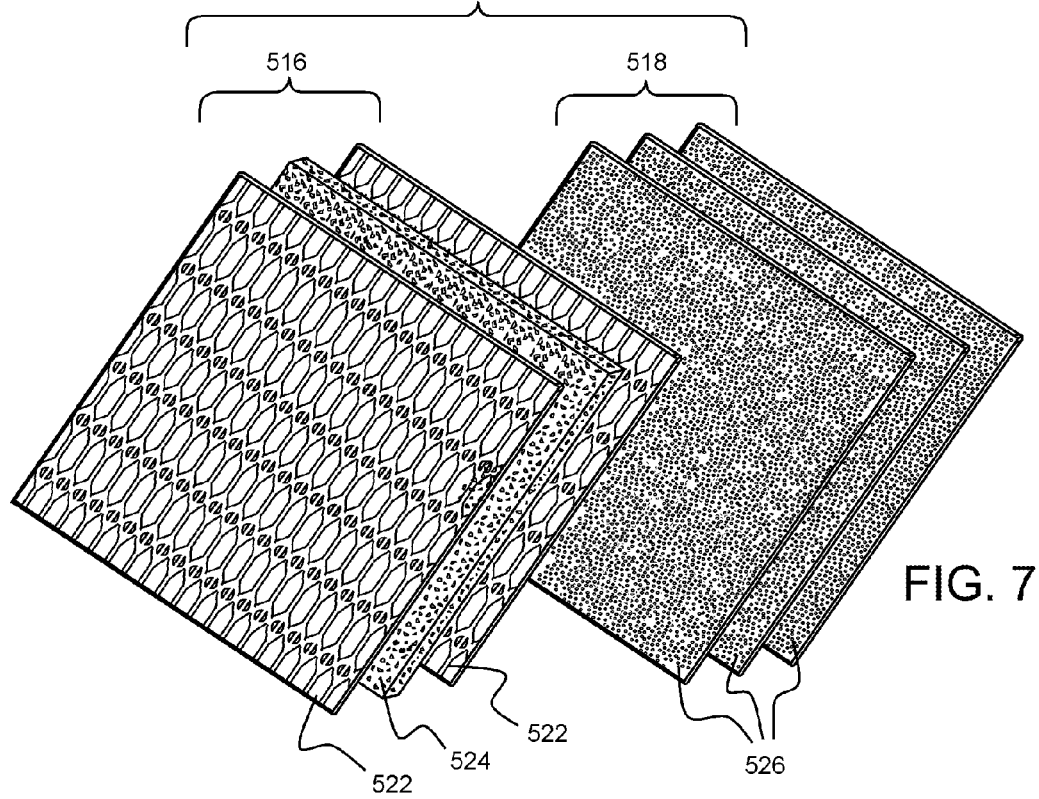
FIG. 7 is an exploded perspective view of the second wave application device of FIGS. 5 and 6.

Referring to FIGS. 5-7, a second wave application device 510 is shown suitable for connection to the electronic stimulation apparatus 200 for delivering electric waves from one of the electronic stimulation devices 10, 110. The second wave application device 510 includes a pouch 512 and a conductive plate 514 held within the pouch 512 which may be removed from the pouch and reinserted therein as shown by arrows 5 of FIG. 6. The conductive plate 514 is preferably fabricated from 6061 aluminum. Alternatively, any suitable conductive material may be used in forming the conductive plate 514. The conductive plate 514 is preferably about 0.4 inch thick, and between about 2 inches wide by 3 inches long and about 3 inches wide by 4 inches long. A male snap connector 560 is connected to a surface of the conductive plate 514. A first side 516 of the pouch 512 preferably includes two layers of a polyester weave material 522 which sandwiches a foam layer 524, which is preferably about 1/16 inch thick. A second side 518 of the pouch 512 preferably includes three layers of microfiber material 526 which is constructed of combined threads of polyester and polyamide. The microfiber material 526 is preferably embedded with silver ion particles to enhance the conductivity and anti-microbial properties of the pouch 512. The components of the first side 516 and the second side 518 are stitched together along a stitch path 520.

During use, two or more wave application devices 510 are preferably attached to the body of a user using a suitable attachment device such as tie wraps, adhesive tapes, or elastic bands. Preferably, the second side 518, which has enhanced conductive properties, is provided in contact with the body of the user such that the first side 516, which is substantially non-conductive, faces up. A snapping connector cable 550 is preferably provided for connection with either the first or second preferred electronic stimulation devices 10, 110 through a stereo connector 552. The snapping connector cable 550 is preferably a medical grade cable with a suitable thermoplastic elastomer surround including Santoprene™ or other suitable polymer. The snapping connector cable 550 includes female snap connectors 554 such as EKG snaps which are preferably attachable to two separate wave application devices 510 in a manner shown by arrow 9 in FIG. 5, whereby current may be conducted from one of the wave application devices 510 to another of the wave application devices 510 and through the body of a user on which the devices 510 are attached. Alternatively, a clipping connector cable 540 including a stereo connector 542 may attach to an edge of the conductive plate 514 via alligator clips 544 as shown by arrow 7 in FIG. 6. In a preferred mode of use, the stereo connector 552 of the snapping connector cable 550 or the stereo connector 542 of the clipping connector cable 540 may be connected to one of the stereo outputs 260 of the electronic stimulation apparatus 200 to provide current output limited to about 1000 microamperes or less through the current limiting transformer 18 of the first preferred electronic stimulation device 10.

Figure 8:
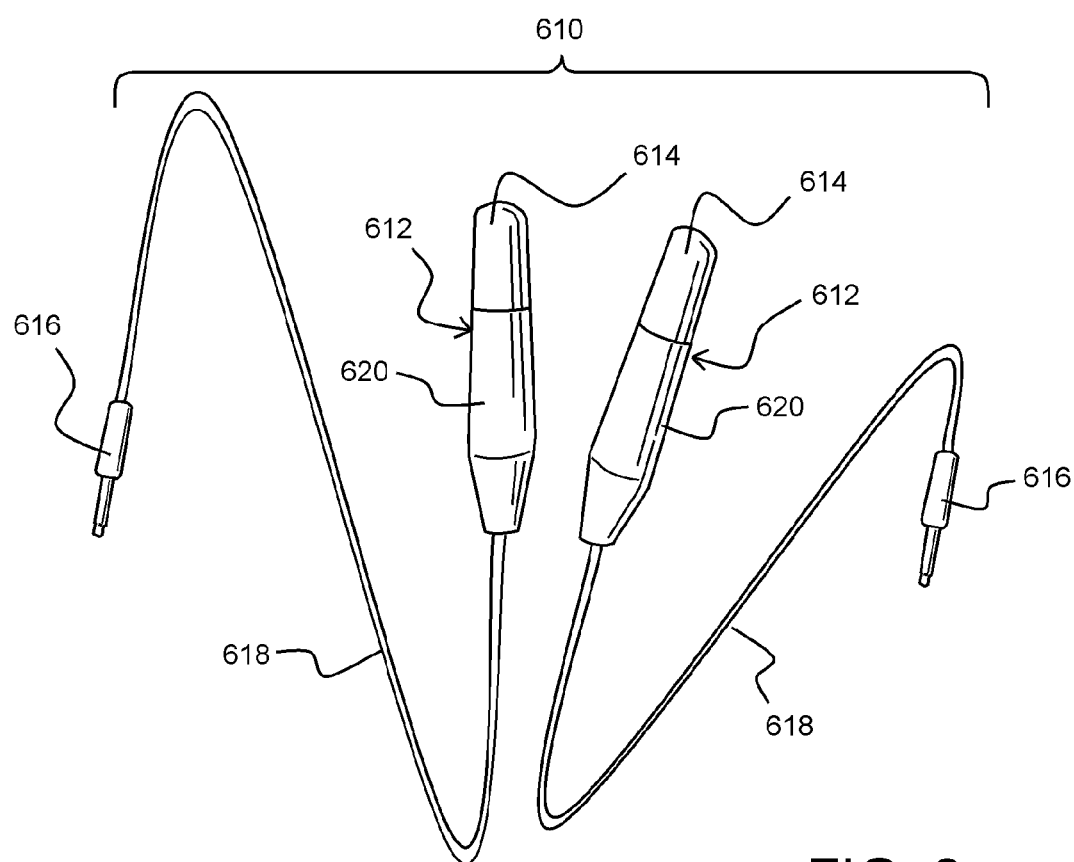
FIG. 8 is a perspective view of a third wave application device according to a preferred embodiment of the present invention.

Referring to FIG. 8 a third wave application device 610 includes a pair of contact cables 612. Each contact cable 612 includes a contact element 614 connected to a mono connector 616 via a wire lead 618. The wire lead 618 is preferably a medical grade cable with a suitable thermoplastic elastomer surround including Santoprene™ or other suitable polymer. The contact element 614 is preferably formed of machined aluminum and is partially encased in a polymeric housing 620 which acts as a handle during use. Alternatively, any suitable conductive material may be used to form the contact element 614. The connectors 616 connect with one or more of the electronic stimulation devices 10, 110, and the contact elements 614 may be contacted on the body of a user to transmit current between the contact elements 614 through the body of the user. In a preferred mode of use, the mono connector 616 of each of the contact cables 612 may be connected to one of the paired mono outputs 361 of the electronic stimulation apparatus 200 to provide current output limited to about 1000 nanoamperes or less through the current limiting transformer 118 of the second preferred electronic stimulation device 110.

Figure 11:
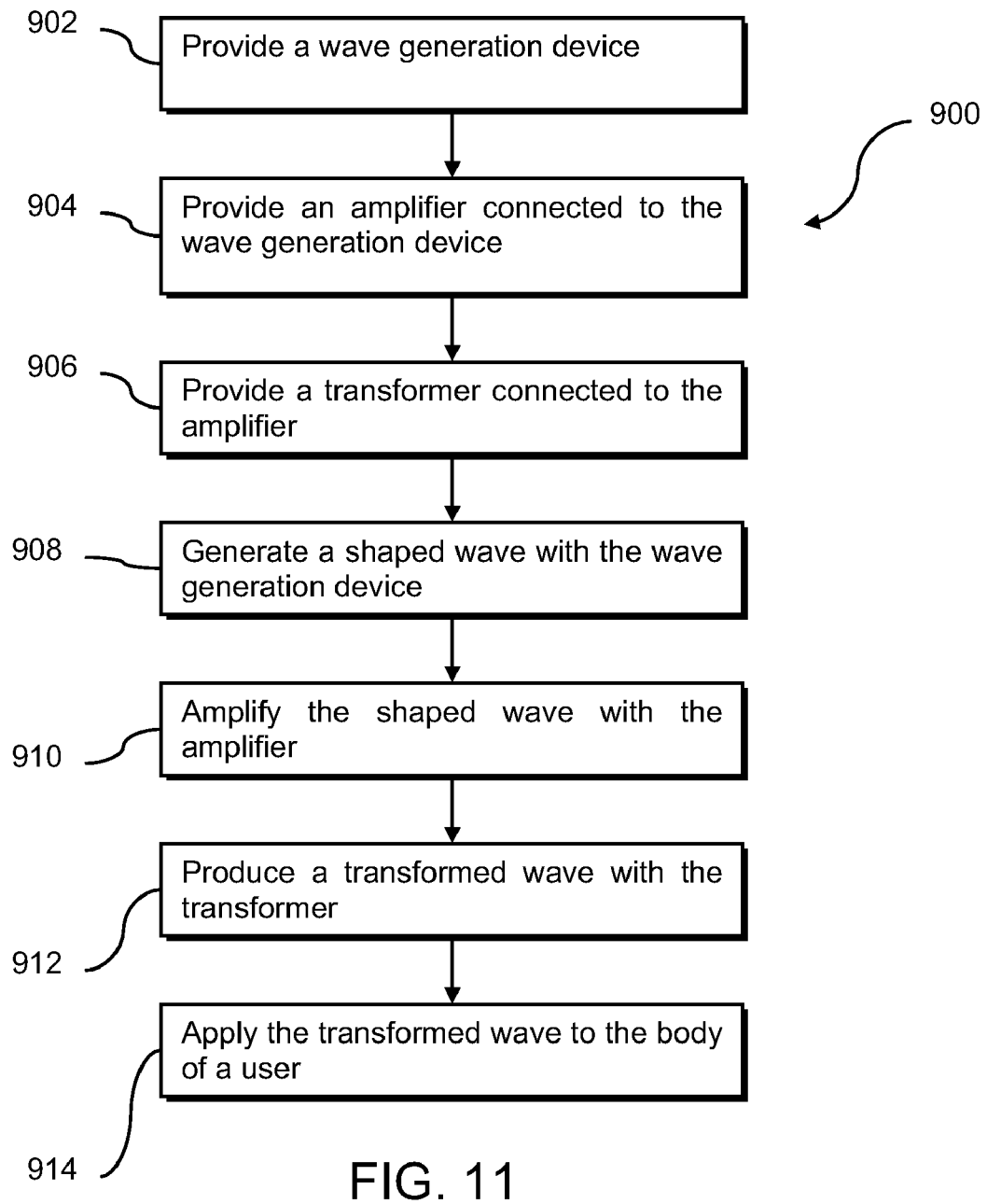
FIG. 11 is a flowchart showing a method for providing electronic stimulation according to a preferred embodiment of the present invention.

Referring to FIG. 11, a method 900 for providing electronic stimulation to a body of a user according to a preferred embodiment of the present invention is shown. The method 900 includes providing a wave generation device (step 902). An amplifier is connected to the wave generation device (step 904), and a current limiting transformer is connected to the amplifier (step 906). A shaped wave is generated with the wave generation device (step 908), and the shaped wave is amplified with the amplifier (step 910). The current limiting transformer is used to produce a transformed wave (step 912), and the transformed wave is applied to a body of a user (step 914).

While the preferred embodiments of the invention have been described in detail above, the invention is not limited to the specific embodiments described above, which should be considered as merely exemplary. Further modifications and extensions of the present invention may be developed, and all such modifications are deemed to be within the scope of the present invention as defined by the appended claims.

What is claimed is:

1. An electronic stimulation device comprising:
   a wave generation device;
   a wave buffer connected to the wave generation device;
   a wave amplifier connected to the wave buffer;
   a transformer connected to the wave amplifier, the transformer configured for connection to leads for transmitting a current through a body of a user; and
   a lead pair connected to the transformer; and
   at least two application devices connected to the lead pair for conducting a current through a body of a user between the two application devices;
   wherein each application device comprises:
      a first sheet of material;
      a second sheet of material comprising at least three layers of threaded polymeric material; and
      a conductive plate disposed between the first sheet of material and the second sheet of material.

2. The electronic stimulation device of claim 1, wherein the wave generation device is configured to produce at least one of square waves, modified square waves, rectangular waves, leading edge buffered waves, and pulses.

3. The electronic stimulation device of claim 1, wherein the wave generation device is configured to produce at least one of square waves, modified square waves, rectangular waves, leading edge buffered waves, and pulses at a frequency less than about 2000 Hz.

4. The electronic stimulation device of claim 3, wherein the transformer is configured for increasing the voltage of a wave transmitted by the amplifier to the transformer by a factor of between about 5 and about 50 times.

5. The electronic stimulation device of claim 3, wherein the transformer is configured for increasing the voltage of a wave transmitted by the amplifier to the transformer by a factor of between about 40 and about 60 times.

6. The electronic stimulation device of claim 1, wherein the transformer comprises a current limiting transformer configured for increasing the voltage of a wave transmitted by the amplifier to the current limiting transformer.

7. The electronic stimulation device of claim 1, wherein a pulse timer control is connected to the transformer for selectively setting a duration of a wave output by the transformer.

8. The electronic stimulation device of claim 1, wherein the wave generation device comprises:
   an AC wave generator;
   a wave shaper connected to the AC wave generator for designating a wave shape; and
   a pulse clock connected to the AC wave generator for timing a designated wave.

9. The electronic stimulation device of claim 8, wherein the AC wave generator is configured to produce a wave having a period of less than approximately 1.5 micro seconds which alternates from positive to negative potential.

10. The electronic stimulation device of claim 1, wherein the wave buffer is configured to receive feedback from the wave amplifier for maintaining wave morphology of a shaped wave generated by the wave generation device.

11. The electronic stimulation device of claim 1, wherein the transformer is a current limiting transformer configured to output current less than about 350 micro amperes.

12. The electronic stimulation device of claim 1, wherein the wave generation device comprises:
   a dual divider for AC wave generation;
   at least one timer connected to the dual divider for providing timing for the wave; and
   at least one multiplexer connected to the dual divider for frequency selection and wave shaping.

13. The electronic stimulation device of claim 1, wherein the wave buffer comprises a diode matrix buffer.

14. The electronic stimulation device of claim 1, further comprising:
   a lead pair connected to the transformer; and
   a glove comprising a plurality of fingers and comprising a plurality of separated contact element pairs connected to the lead pair for conducting a current between the contact element pairs through a body of a user.

15. The electronic stimulation device of claim 14, wherein at least one of the fingers of the glove comprises at least one of the plurality of separated contact element pairs.

16. The electronic stimulation device of claim 1, wherein:
   at least one of the at least three layers of threaded polymeric material comprises silver ion particles.

17. The electronic stimulation device of claim 16, wherein each of the at least two sponges comprises a flexible metallic plate attached thereto for conducting a current therethrough.

18. A method for providing electronic stimulation to a body of a user comprising:
   providing at least one wave generation device;
   providing at least one wave amplifier connected to the at least one wave generation device;
   providing at least one current limiting transformer connected to the at least one amplifier;
   providing a lead pair connected to the at least one current limiting transformer; and
   providing at least two application devices connected to the lead pair for conducting a current through a body of a user between the two application devices;
   wherein each application device comprises:
      a first sheet of material;
      a second sheet of material comprising at least three layers of threaded polymeric material; and
      a conductive plate disposed between the first sheet of material and the second sheet of material;
   generating a shaped wave with the at least one wave generation device;
   amplifying the shaped wave with the at least one amplifier;
   using the at least one current limiting transformer to produce a transformed wave; and
   applying the transformed wave to a body of a user using the application device;
   alternately applying the transformed wave to the body of the user for a duration of less than 10 seconds on and less than 10 seconds off.

19. The method of claim 18, further comprising producing the transformed wave with a voltage higher than that of the shaped wave using the at least one current limiting transformer.

20. The method of claim 19, further comprising producing the transformed wave with a voltage stepped up by a factor of between about 5 and 50 times from that of the shaped wave using the at least one current limiting transformer.

21. The method of claim 19, further comprising producing the transformed wave with a voltage stepped up by a factor between about 40 and 60 times from that of the shaped wave using the at least one current limiting transformer.

22. The method of claim 18, further comprising:
   producing a first set of the transformed wave comprising a current between about 0 microamperes and 1000 microamperes; and
   producing a second set of the transformed wave comprising a current between about 0 nanoamperes and 1000 nanoamperes;

applying the first set of the transformed wave to the body of the user; and applying the second set of the transformed wave to the body of the user.

23. The method of claim 18, further comprising generating the shaped wave as at least one of a square wave, modified square wave, rectangular wave, leading edge buffered wave, and pulses at a frequency less than about 2000 Hz.

24. The method of claim 18, further comprising buffering the shaped wave to maintain wave morphology during the step of amplifying the shaped wave.

25. The method of claim 18, further comprising limiting a current amplitude of the transformed wave to less than about 350 micro amperes with the at least one current limiting transformer.

26. An electronic stimulation device comprising:
a power supply;
at least one wave generation device;
a first current limiting transformer connected to the at least one wave generation device, the first current limiting transformer configured for producing a first transformed wave comprising a first current between about 0 microamperes and 1000 microamperes and configured for connection to leads for transmitting the first current through a body of a user;
a second current limiting transformer connected to the at least one wave generation device, the second current limiting transformer configured for producing a second transformed wave comprising a second current between about 0 nanoamperes and 1000 nanoamperes and configured for connection to leads for transmitting the second current through the body of the user;
a pulse timer control configured for setting an on time and an off time of at least one of the first transformed wave and the second transformed wave;
a lead pair connected to the first current limiting transformer and the second current limiting transformer; and
at least two application devices connected to the lead pair for conducting a current through a body of a user between the two application devices;

wherein each application device comprises:
a first sheet of material;
a second sheet of material comprising at least three layers of threaded polymeric material; and
a conductive plate disposed between the first sheet of material and the second sheet of material.

27. The electronic stimulation device of claim 26, wherein the at least one wave generation device is configured to output wave frequencies of at least one of about 201 Hz, 403 Hz, 604 Hz, 1004 Hz, 1256 Hz, 20 Hz, 500 Hz, 900 Hz, 1000 Hz and 1100 Hz.

28. The method of claim 18, further comprising generating the shaped wave as an extended pulse which alternates from a from a first voltage to a second voltage, the second voltage being of approximately the same magnitude as the first voltage but opposite in sign.

29. The method of claim 28, wherein the pulse extends for a period of approximately 0.40 seconds.

30. The method of claim 28, wherein the first voltage is approximately 8.5 Volts.

31. The method of claim 18, further comprising selectively alternately applying the transformed wave to the body of the user for a duration of between 1 and 6 seconds on and between 1 and 6 seconds off.

32. The electronic stimulation device of claim 1, wherein the first sheet of material comprises:
at least two layers of a polymeric weave material; and
a foam layer disposed between the at least two layers of the polymeric material.

33. The electronic stimulation device of claim 1, wherein the first sheet of material and the second sheet of material are configured to form a pocket, and wherein the conductive plate is removably received within the pocket.

34. The electronic stimulation device of claim 1, wherein conductive plate comprises a snap connector for removable connection to the leads.

* * * * *